United States Patent
Brown (10) Patent No.: US 9,259,270 B2
(45) Date of Patent: Feb. 16, 2016

(54) APPARATUS AND METHOD FOR DETECTING OVERHEATING DURING LASER SURGERY

(76) Inventor: Joe Denton Brown, Panama City, FL (US)

(*) Notice: Subject to any disclaimer, the term of this patent is extended or adjusted under 35 U.S.C. 154(b) by 53 days.

(21) Appl. No.: 13/127,911

(22) PCT Filed: Nov. 6, 2009

(86) PCT No.: PCT/US2009/006021
§ 371 (c)(1),
(2), (4) Date: May 5, 2011

(87) PCT Pub. No.: WO2010/053575
PCT Pub. Date: May 14, 2010

(65) Prior Publication Data
US 2011/0213349 A1    Sep. 1, 2011

Related U.S. Application Data

(60) Provisional application No. 61/193,231, filed on Nov. 7, 2008, provisional application No. 61/173,799, filed on Apr. 29, 2009, provisional application No. 61/183,334, filed on Jun. 2, 2009, provisional application No. 61/232,314, filed on Aug. 7, 2009.

(51) Int. Cl.
| | |
|---|---|
| *A61B 18/24* | (2006.01) |
| *A61B 18/22* | (2006.01) |
| *A61B 17/00* | (2006.01) |
| *G01J 1/04* | (2006.01) |
| *A61N 5/06* | (2006.01) |

(52) U.S. Cl.
CPC ....... *A61B 18/22* (2013.01); *A61B 2017/00057* (2013.01); *A61B 2017/00084* (2013.01); *A61B 2017/00119* (2013.01); *A61B 2218/008* (2013.01); *A61N 5/0601* (2013.01); *A61N 2005/063* (2013.01); *A61N 2005/0628* (2013.01); *G01J 1/0425* (2013.01); *G01J 1/0459* (2013.01)

(58) Field of Classification Search
USPC ............................... 606/7, 11–16; 607/88–94
See application file for complete search history.

(56) References Cited

U.S. PATENT DOCUMENTS

| | | |
|---|---|---|
| 3,912,362 A | 10/1975 | Hudson |
| 4,060,308 A | 11/1977 | Barnoski et al. |
| 4,385,832 A | 5/1983 | Doi et al. |
| 4,474,429 A | 10/1984 | Yoldas et al. |
| 4,519,390 A | 5/1985 | Horne |

(Continued)

FOREIGN PATENT DOCUMENTS

WO   PCT/US2009/01417   *   3/2009

*Primary Examiner* — William Thomson
*Assistant Examiner* — Jeffrey Lipitz
(74) *Attorney, Agent, or Firm* — Bacon & Thomas, PLLC (57) ABSTRACT

A method and apparatus for improving the safety of a surgical procedure involving delivery of laser energy to a tissue, involves enhancing or increasing the detectability of radiation emitted by the tissue or any portion of a surgical instrument or device by providing a sacrificial material that absorbs radiation emitted during the surgical procedure, increasing the temperature of a surface on which the material is disposed and/or causing damage radiation to be emitted in a way that can be detected by monitoring the temperature of the surface and/or radiation, including infrared and/or visible light, emitted by the surface. In a preferred embodiment of the invention, the radiation absorbing material is a sheath arranged to surround the fiber.

16 Claims, 5 Drawing Sheets

(56) References Cited

U.S. PATENT DOCUMENTS

| | | | |
|---|---|---|---|
| 4,543,477 A | 9/1985 | Doi et al. | |
| 4,575,181 A | 3/1986 | Ishikawa | |
| 4,669,465 A | 6/1987 | Moore et al. | |
| 4,678,273 A | 7/1987 | Vilhelmsson | |
| 4,718,417 A | 1/1988 | Kittrell et al. | |
| 4,737,011 A | 4/1988 | Iri et al. | |
| 4,760,845 A | 8/1988 | Kovalcheck | |
| 4,762,385 A | 8/1988 | Fuse | |
| 4,784,466 A | 11/1988 | Khoe et al. | |
| 4,832,024 A | 5/1989 | Boussignac et al. | |
| 4,883,054 A | 11/1989 | Fuller et al. | |
| 4,883,342 A | 11/1989 | Ishii et al. | |
| 4,913,142 A | 4/1990 | Kittrell et al. | |
| 4,994,059 A | 2/1991 | Kosa et al. | |
| 5,009,655 A * | 4/1991 | Daignault, Jr. | A61B 18/28 606/10 |
| 5,057,099 A | 10/1991 | Rink | |
| 5,061,265 A | 10/1991 | Abela et al. | |
| 5,098,427 A | 3/1992 | Hessel et al. | |
| 5,101,457 A | 3/1992 | Blonder et al. | |
| 5,132,079 A | 7/1992 | Stewart et al. | |
| 5,154,707 A | 10/1992 | Rink et al. | |
| 5,179,610 A | 1/1993 | Milburn et al. | |
| 5,196,005 A | 3/1993 | Doiran et al. | |
| 5,219,345 A | 6/1993 | Potter | |
| 5,243,681 A | 9/1993 | Bowen et al. | |
| 5,274,721 A | 12/1993 | Dickinson et al. | |
| 5,291,570 A | 3/1994 | Filgas et al. | |
| 5,299,141 A | 3/1994 | Hungerford et al. | |
| 5,300,066 A | 4/1994 | Manoukian et al. | |
| 5,330,465 A | 7/1994 | Doiron et al. | |
| 5,354,323 A | 10/1994 | Whitebook | |
| 5,490,227 A | 2/1996 | Tanabe et al. | |
| 5,569,240 A | 10/1996 | Dowlatshahi et al. | |
| 5,619,602 A | 4/1997 | Sandrstom et al. | |
| 5,649,923 A | 7/1997 | Gregory et al. | |
| 5,662,712 A * | 9/1997 | Pathak | A61F 2/945 606/195 |
| 5,820,627 A | 10/1998 | Rosen et al. | |
| 5,829,445 A | 11/1998 | Martin et al. | |
| 5,928,222 A | 7/1999 | Kleinerman | |
| 5,946,437 A | 8/1999 | Uchida et al. | |
| 5,948,260 A * | 9/1999 | Attaway et al. | 210/603 |
| 5,968,033 A | 10/1999 | Fuller et al. | |
| 6,154,596 A | 11/2000 | Sandstrom et al. | |
| 6,282,349 B1 * | 8/2001 | Griffin | G02B 6/3813 385/81 |
| 6,389,307 B1 | 5/2002 | Abela | |
| 6,398,777 B1 | 6/2002 | Navarro et al. | |
| 6,530,921 B1 * | 3/2003 | Maki | 606/15 |
| 6,966,906 B2 * | 11/2005 | Brown | 606/15 |
| 7,204,645 B2 | 4/2007 | Brown | |
| 2002/0045811 A1 * | 4/2002 | Kittrell et al. | 600/407 |
| 2002/0068963 A1 | 6/2002 | Maki et al. | |
| 2003/0023236 A1 | 1/2003 | Gowda et al. | |
| 2004/0006333 A1 | 1/2004 | Arnold et al. | |
| 2004/0092913 A1 | 5/2004 | Hennings et al. | |
| 2004/0147912 A1 | 7/2004 | Sinofsky | |
| 2004/0147913 A1 | 7/2004 | Sinofsky | |
| 2004/0162490 A1 | 8/2004 | Soltz et al. | |
| 2004/0249261 A1 | 12/2004 | Torchia et al. | |
| 2005/0038419 A9 | 2/2005 | Arnold et al. | |
| 2005/0124985 A1 | 6/2005 | Takayama et al. | |
| 2005/0131400 A1 * | 6/2005 | Hennings | A61B 18/24 606/15 |
| 2005/0267452 A1 | 12/2005 | Farr et al. | |
| 2005/0273090 A1 | 12/2005 | Nieman et al. | |
| 2005/0288654 A1 | 12/2005 | Nieman et al. | |
| 2005/0299655 | 12/2005 | Root et al. | |
| 2006/0052661 A1 | 3/2006 | Gannot et al. | |
| 2006/0122587 A1 | 6/2006 | Sharareh | |
| 2006/0217692 A1 | 9/2006 | Nauberger | |
| 2006/0217693 A1 | 9/2006 | Gowda et al. | |
| 2006/0253178 A1 | 11/2006 | Masotti | |
| 2007/0049911 A1 * | 3/2007 | Brown | 606/12 |
| 2007/0142881 A1 * | 6/2007 | Hennings | A61B 18/203 607/89 |
| 2008/0308753 A1 * | 12/2008 | Stuba et al. | 250/504 R |
| 2009/0062782 A1 | 3/2009 | Brown | |
| 2009/0149845 A1 | 6/2009 | Brown | |

\* cited by examiner

APPARATUS AND METHOD FOR DETECTING OVERHEATING DURING LASER SURGERY

This application claims the benefit of U.S. Provisional Patent Application Ser. Nos. 61/193,231, filed Nov. 7, 2008; 61/173,799, filed Apr. 30, 2009; 61/183,334, filed Jun. 2, 2009; and 61/232,314 filed Aug. 7, 2009.

BACKGROUND OF THE INVENTION

1. Field of the Invention

This invention relates to various improvements to the methods and apparatus disclosed in U.S. Patent Publication Nos. 2009/0062782 and 2009/0149845, and other similar laser treatment methods and apparatus involving monitoring of the treatment site for conditions such as overheating. The improvements include:

a. Provision of a structural element made of a material that absorbs selected wavelengths of radiation emitted during the surgical procedure, and that in response heats up or emits radiation in a way that can more easily and reliably be detected by the treatment site monitoring arrangement, whether by monitoring radiation transmitted back through the laser deliver conduit or fiber, or by a sensor or detector at the treatment site;

b. Use of other coatings to enhance detection, such as inclusion of a dark coating material to increase contrast between parts of an instrument that are overheating and other parts of the instrument;

c. Positioning of a overheating detector of the type disclosed in the parent application on a bare fiber rather than in an introducer or catheter; and d. Provision of an improved treatment site monitoring method.

The above listed improvements may be used separately or in any combination with each other or with any elements of the system disclosed in U.S. Patent Publication Nos. 2009/0062782 and 2009/0149845, or in combination with other surgical laser methods and systems, including those described in U.S. Patent Publication Nos. 2009/0062782 and 2009/0149845 as prior or related art. While the methods and apparatus of the invention may be used with a variety of surgical laser procedures, it is especially useful for urological and varicose vein treatment applications where thermal runaway has been a particular problem.

The structural element of the invention may be disposed in or integrated with an instrument, such as a coating on an endoscope, introducer, or any other instrument present at a location where overheating might occur. Alternatively, the structural element may be a discrete element such as a sheath that can be inserted into the instrument or disposed to protect any part of the instrument and/or tissues at the treatment site. If the structural element is a sheath, then the sheath may be arranged to be inserted into an endoscope with the fiber withdrawn slightly into the sheath, thereby protecting the working channel of the endoscope from mechanical damage from the relatively sharp tip of the fiber without interfering with movement of the fiber.

In addition, the apparatus of the invention may include or be used with components for monitoring radiation absorption by the radiation absorbing structural element, either by monitoring the temperature of the radiation absorbing structural element, or by monitoring radiation emitted by the structural element.

Still further, a support guide may be added to ensure that the fiber tip avoids contact with the working channel of an instrument such as an introducer or endoscope.

2. Description of Related Art

A number of copending patent applications, prior patents, and prior publications, address the problem of detecting and preventing damage due to overheating of tissues and/or instruments/devices used to deliver laser energy to tissues during laser surgery or therapeutic laser procedures. For example, U.S. Patent Publication No. 2009/0062782 (based on U.S. patent application Ser. No. 12/047,819) discloses a safety feedback control unit in which radiation resulting from overheating at the location of the surgery is detected and used to control fiber position, laser activation, or rate of pullback. U.S. Patent Publication No. 2009/0149845 (based on U.S. patent application Ser. No. 12/073,922) discloses a radiation feedback system in which a sensor at the treatment end of the fiber monitors wavelengths indicative of temperature at the treatment end so that overheating of tissues can be detected before the flash of light from pyrolytic burning occurs, and monitoring of the output of the laser by downstream deflection, absorption, or fiber movement in response to overheating detection. Many of the principles disclosed in U.S. Patent Publication Nos. 2009/0062782 and 2009/0149845 have been implemented in the LaserGuard™ system made by Optical Integrity, Inc. of Panama City, Fla.

One feature of the LaserGuard™ system is that it not only seeks to detect damage radiation from overheated tissues or instruments/devices, but also to enhance sampling detection by slightly bending a fiber anywhere along the fiber to leak non-coherent radiation caused by overheating and thereby detect the overheating while minimizing losses to the laser transmission are kept to a minimum. However, while the LaserGuard™ system has been effective in detecting overheating in a variety of laser surgery applications so as to prevent injury to the patient and protect other devices such as stone baskets and stone cones, it has been found that some treatment applications are still subject to overheating or burning of tissues, and that the likelihood of problems increases with the number of times a particular instrument is used. This is a critical problem given the cost of surgical instruments and the need to hold down costs if at all possible without sacrificing the safety of the patient.

The inventor has investigated the cause of continued overheating problems, even in systems with temperature or damage radiation feedback, and found that the cause can in many cases be traced to erosion or wear at the tips of the laser delivery instruments. This is particularly true where transmissive caps are provided at the end of the fiber, either to prevent fiber contact with tissues or to preserve the glass to air interface in a liquid environment. Unfortunately, the fiber cap surface erodes quickly when the fiber tip is buried into the tissue causing the temperature to rise. When that temperature exceeds 1000 degrees C., the cap absorbs infrared radiation due to free electron absorption, which can quickly erode the cap's surface and allow water into the cap destroying the glass to air interface. Continued lasing heats the water in the cap until the cap blows off like a bullet, sometimes lodging into surrounding tissue requiring surgical extraction.

It would seem that a feedback detection system should be able to detect the overheating before the cap is blown off. However, the feedback system has trouble detecting contact with a foreign surface because the surface prevents the damage radiation from reaching the detector, and therefore the amount of damage radiation available to the detector is relatively small. For example, if a partially transmitting surface is surrounded by a temperature conductive surface such as a tissue, much of the damage radiation will be absorbed by the conductive surface, and therefore will not reach the detector in time to enable termination or modulation of the laser energy being delivered and prevent damage caused by the overheating.

This invention addresses the problem of incomplete or delayed detection of overheating by providing sacrificial elements such as coatings or sheaths arranged to absorb damage radiation and emit warning radiation before the damage radiation would otherwise be detected by direct monitoring. In addition, coatings may be provided to enhance the detection of warning or damage radiation by, for example, increasing the contrast between the radiation to be detected and background radiation.

With respect to the embodiment in which the sacrificial element is a coating, those skilled in the art will appreciate that instrument coatings are known in the art. For example, U.S. Patent Publication No. 2009/0149845 mentions coating of the working channel of the catheter or introducer with Teflon™ or a similar protective material, so that an overheating fiber may be withdrawn into the working channel where damage will be minimal due to the protective effect of the coating. However, the known coatings are intended to be survive the treatment procedure, rather than being sacrificed before damage actually occurs.

With respect to the embodiment in which the sacrificial element takes the form of a sheath that surrounds the laser delivery fiber and serves to mechanically protect the instrument through which the fiber is inserted into the patient, the "sheath" of this embodiment differs from the conventional sheath in that it is designed to avoid affecting insertion of the fiber into the scope. Instead, its purpose is solely to absorb specific wavelengths of radiation in order to enhance detection of the radiation.

Those skilled in the art will of course appreciate that "sheaths" have long been used to protect surgical instruments inserted into a patient. For example, LISA Laser Products OHG of Katlenburg-Lindau, Germany sells disposable fiber insertion sheaths under the tradename FlexGuard™, which are used to guide fibers along a path established by bending the sheath, which remains deflected during insertion of the laser fiber. These sheaths are not suitable for use in connection with the present invention, and do not correspond to the sheaths described herein, not only because they are not designed to burn away upon overheating, thereby amplifying damage radiation, but also because the sheaths of the present invention are designed to be as flexible as possible so as not to interfere with positioning of the fiber.

In order to carry out the function of absorbing specific wavelengths of radiation while still maintaining flexibility, the sheath of the present invention must be relatively thin, whereas the FlexGuard™ sheaths must be thick enough to hold a particular shape when bent, and also to protect the inside of the working channel of a ureterorenoscope into which the fiber is inserted, as explained in LISA Laser Products product literature on the FlexGuard™ sheaths and in LISA Laser's U.S. Pat. No. 6,572,608. Unlike FlexGuard™, the sheath of the preferred embodiment is easily inserted at the same time as the fiber and therefore does not have the same limitations such as decreased water flow and loss of deflection because the scope is already in position and the fiber acts as a means to stiffen the polyimide or PET sheath.

The FlexGuard™ sheath is not the only prior sheath. Protective sheaths have been used in a variety of surgical applications, to protect optical fibers and other instruments such as the Nitinol shape memory instruments described in U.S. Pat. No. 6,966,906 (Brown) and U.S. Pat. No. 6,706,053 (Boylan), but none of the prior sheaths is designed to be sacrificed upon overheating in order to increase the detectability of damage radiation emitted during the overheating.

SUMMARY OF THE INVENTION

It is accordingly a first objective of the invention to provide improved methods and apparatus for minimizing damage caused by overheating at the distal end of a therapeutic or surgical energy delivery device.

It is a second objective of the invention to provide a method and apparatus for rapidly and reliably detecting any overheating at a treatment site.

It is a third objective of the invention to provide a treatment site monitoring method and apparatus that is capable of detecting damage radiation resulting from contact between tissues and a surgical instrument, even when the damage radiation is partially obscured, blocked, absorbed, or attenuated by the tissues.

It is a fourth objective of the invention to provide a treatment site monitoring method that improves detection of overheating at a treatment site, and that does not interfere with conventional surgical procedures such as insertion of a laser deliver fiber into an endoscope, and irrigation of the treatment site.

These objectives, which should be taken as exemplary in nature rather than limiting, are achieved by providing a radiation absorbing element that in effect serves as a sacrificial element to limit damage to a surface being protected. For example, the sacrificial element may be a fiber sheath that surrounds the laser deliver fiber, the sheath being made of a material that is highly absorptive to selected wavelengths of laser radiation so as to provide the sacrificial surface. Alternatively, in place of the thin clear plastic clad of a conventional endoscope working channel, a radiation absorbing element in the form of a metal heat conductive clad may be provided, thereby making the working channel highly absorptive to the laser radiation and causing a fast rise in temperature should overheating occur as a result of contact between the fiber and a tissue. It is of course within the scope of the invention to dispose the radiation-absorbing element or material on any surface that receives damage radiation, rather than just in the working channel of an endoscope, and to not only arrange the material to form a sheath or metal clad, but also to dispose the material as a sleeve, coating, layer, and so forth. Still further, the structural element may be integrated with or form a part of the instrument to be protected. Finally, the structural element may also be disposed adjacent a tissue to be protected, for example where fine laser ablation is required, rather than in or at an instrument.

In an especially preferred embodiment of the invention, the radiation absorbing sacrificial element is a sacrificial sheath in the form of a relatively thin tubing material supported by a laser-delivery optical fiber, which is to be distinguished from a conventional sheath that provides support for the fiber and therefore is relatively thick and not as flexible. The material of the sheath is preferably a material such as polyimide or polyethylene terephthalate (PET) that will not limit movement of the fiber or block irrigation fluid from passing through a conduit in which the fiber and sheath have been inserted. For example, the sheath may have a thickness of less than 500 microns (compared to a typical fiber thickness of 200 microns).

In case the sheath is to be used in applications involving an endoscope or introducer, the sacrificial fiber sheath of the preferred embodiment has the further advantage, relative to a coating or other radiation absorbing structural element, of protecting the working surface of an endoscope or introducer in which the fiber is inserted, as well as preventing contact between the fiber and a tissue when the fiber is outside the working channel or used without an endoscope or introducer, thus preventing overheating in the first place.

In a specific exemplary implementation of the invention, described below in connection with the drawings, the invention provides an optical fiber protective device having the following advantages or properties:

- The device protects endoscopes from mechanical and or heat damage from laser fibers during surgical procedures and, in a preferred embodiment, consists of a section of tubing (polyimide, PET, or other) that fits over a laser fiber that when assembled together is inserted into an endoscope for use in surgical procedures;
- The device includes fittings that permit the sheath to be locked onto the fiber so that the sheath and fiber are moved simultaneously or unlocked from the fiber so that the sheath and fiber can be moved independently;
- The device also includes fittings permitting the sheath to be locked into an endoscope;
- The device may optionally also feature an adjustment mechanism permitting the ability to adjust the length of the sheath that is in the endoscope. Such adjustment will allow the surgeon to extend the sheath into the field of view providing a safety margin from the distal tip of the endoscope.
- The device is also designed so that the fiber and sheath can be inserted into a flexed endoscope without damage to the scope.
- An additional design feature is that a further heat shrink feature may be included, in the form of a sleeve that will shrink when heated so that it will trap sheath and the tip of a fiber that is drawn back into the scope while the laser is being fired into the fiber.

Although the damage radiation detection enhancing method and apparatus of the invention, and the radiation absorption increasing surfaces or sheaths used to implement those methods, may be used in connection with the feedback systems and methods disclosed in U.S. Patent Publication Nos. 2009/0062782 and 2009/0149845, as well as the LaserGuard™ system sold by Optical Integrity, Inc., those skilled in the art will appreciate that the method and apparatus of the invention may be used in connection with other feedback systems and methods, and is not intended to be limited in application to a particular type of sensor, detector, or feedback method or apparatus.

It should also be appreciated that the term "surgical instrument" as used herein encompasses any device or manmade object or part that is inserted into a patient, including a laser delivery fiber and any devices or parts used to facilitate insertion of the fiber, such as an endoscope or introducer. It will be appreciated that the "overheating" detected by the method and apparatus of the invention may encompass overheating of tissues or any portion of a surgical instrument that, if undetected, could eventually result in injury to the patient or damage to the instrument. Further, it is to be understood that while particular surgical procedures may be mentioned herein, the invention is not to be limited to any particular surgical procedure, but rather should encompass any surgical procedure in which radiation is delivered to a treatment site by an instrument inserted into the patient to a position near the treatment site. These procedures include, but are not limited to, those involving urological stone removal or destruction, vascular treatment, and laser liposuction.

Finally, the present invention provides for the addition of a support guide to ensure that the fiber tip avoids contact with a working channel into which the fiber tip has been withdrawn. The support guide may be mounted on a sheath as described above, or directly on the fiber.

DETAILED DESCRIPTION OF THE PREFERRED EMBODIMENTS

Figure 1:
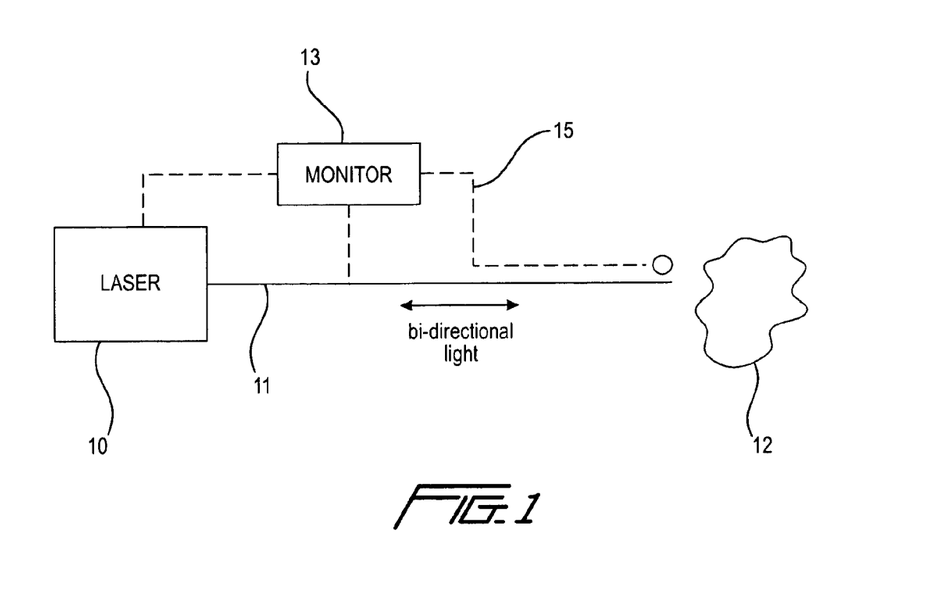
FIG. 1 is a schematic diagram of a conventional laser treatment and feedback system to which the principles of the invention may be applied.
Figure 2:
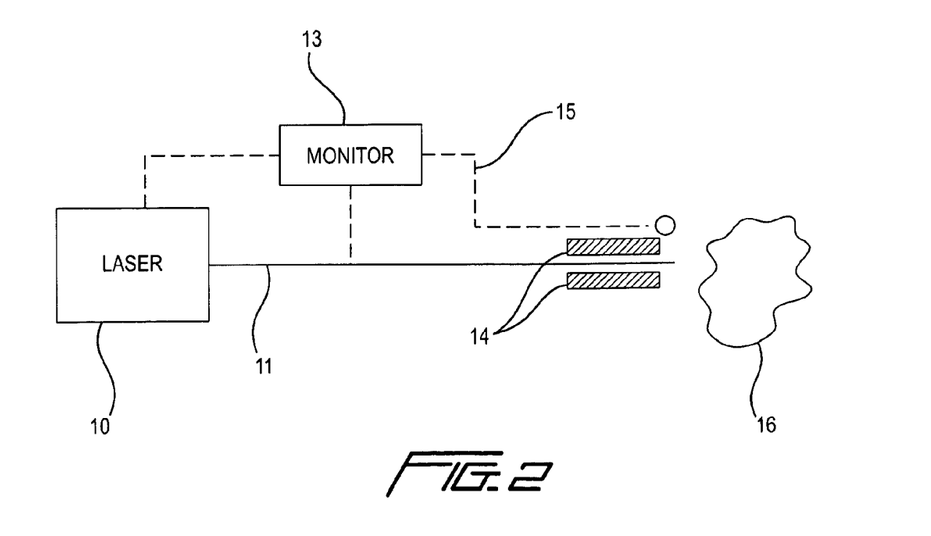
FIG. 2 is a schematic diagram showing the manner in which the system of FIG. 1 is modified according to the principles of the invention.

The principles of the invention may be understood by a comparison between FIG. 2, which is a schematic illustration of an existing temperature or radiation monitoring feedback system, and FIG. 2, which shows a modification of the system of FIG. 1.

The feedback system illustrated in FIG. 1, which generally corresponds to the system disclosed in copending U.S. patent application Ser. No. 12/073,922, cited above, includes a laser 10 arranged to supply radiation to an optical fiber 11 for delivering energy to the treatment site. Radiation emitted at the treatment site may be in the form of infrared radiation or, in the case of actual burning, visible light. A monitor 13 is arranged to detect the radiation in a number of different ways, such as by detecting visible light transmitted back through the same fiber that supplies the laser energy to the treatment site, or by a separate detector and feedback path 15 having a sensor or detector for either radiation or temperature. When the monitor detects that overheating has occurred or is imminent, an audible or visible alert is provided to an operator of the laser, and/or a feedback signal is supplied to the laser to either modulate or terminate the laser output.

The monitor 13 illustrated in FIGS. 1 and 2 may be placed anywhere where it can detect overheating, including directly on the fiber. While an introducer, catheter, sheath or the like will be preferred for many applications, there are also applications in which a bare fiber may be inserted into the patient. By placing the detector directly on the fiber, the safety of such applications is enhanced, possibly even eliminating the need for an introducer in applications where an introducer would normally be used.

As discussed above, in the arrangement shown in FIGS. 1 and 2, damage radiation may be difficult to detect due to interference from tissues surrounding or between the detector and the site of the damage. To solve this problem, the invention provides a sacrificial element 14 for absorbing selective radiation wavelengths 16. The sacrificial element 14 may be in the form of a coating on a surface exposed to the damage radiation, such as the working channel of an endoscope, may be integrated with or form a part of the surface to be protected, or may be a discrete element that can be disposed near a surface or tissue to be protected. In the preferred embodiment illustrated in FIGS. 3-8, for example, the sacrificial element 14 takes the form of a sheath into which the laser delivery fiber is inserted, and that is inserted together with the laser delivery fiber into an endoscope.

Any radiation absorbing material that has the effect of amplifying or enhancing selected wavelengths of damage radiation so that it can more easily be detected may be used as the sacrificial element 14 of FIG. 2. As the sacrificial element 14 absorbs selected wavelengths of the damage radiation 12, it emits additional radiation 13 and/or increases in temperature for detection using bi-directional light or a separate feedback path.

Figure 3:
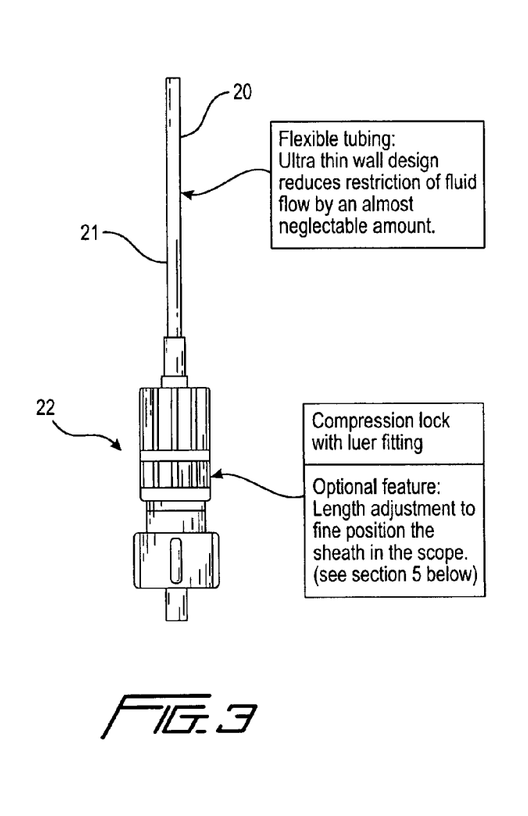
FIG. 3 is a side view of a sacrificial sheath arrangement constructed according to the principles of a preferred embodiment of the invention.

Turning to FIG. 3, the sacrificial element 14 schematically illustrated in FIG. 2 is embodied by a protective sheath 20 made of flexible ultra thin wall tubing 21 with an adjustable compression lock and luer fitting 22 for easy connection to the working channel port on an endoscope (not shown). Compression locks and luer fittings are well-known and commonly used to connect medical tubing to endoscopes, catheters, and other instruments, and the invention is not to be limited to a particular compression lock, luer fitting, and/or other tubing connection arrangement.

As indicated above, the material of the tubing 21 must be flexible, relatively thin, and capable of absorbing heat or radiation and responsively emitting radiation or increasing in temperature in a way that can be monitored by a suitable sensor or detector. One suitable material for the tubing is polyimide, although materials such as polyethylene terephthalate (PET) or other flexible plastics may be substituted. Unlike the conventional sheath, which typically has a wall thickness of 0.9 mm, the tubing of the invention is preferably substantially thinner, so as not to interfere with insertion of the fiber and tubing into a scope, or limit flow of water or other irrigation fluid through the scope, but without affecting the structural integrity of the sheath. In the case of polyimide, a thickness of less than 0.5 mm, such as 430 microns, can be used.

Optionally, the sheath may include holes or perforations (not shown) along its length to allow for better gas sterilization and aid in providing fluid access to help lubricate the fiber so as to ease movement of the fiber within the sheath.

In addition to or instead of the sacrificial element, whether in the form of a coating, sheath, or other element, the present invention also may utilize a detection enhancing element, for example by modifying the color or properties of the Teflon™ or other protective coating that is conventionally provided in the working channel of the introducer to increase contrast and/or minimizes reflections to increase the probability of detecting the glow caused by overheating. Alternatively, instead of a detection-enhancing coating or material, the working channel of the introducer may include a black or dark colored inner sheath, which may be permanent or disposable, that increases contrast or minimizes reflections to further enhance detection.

Figure 4:
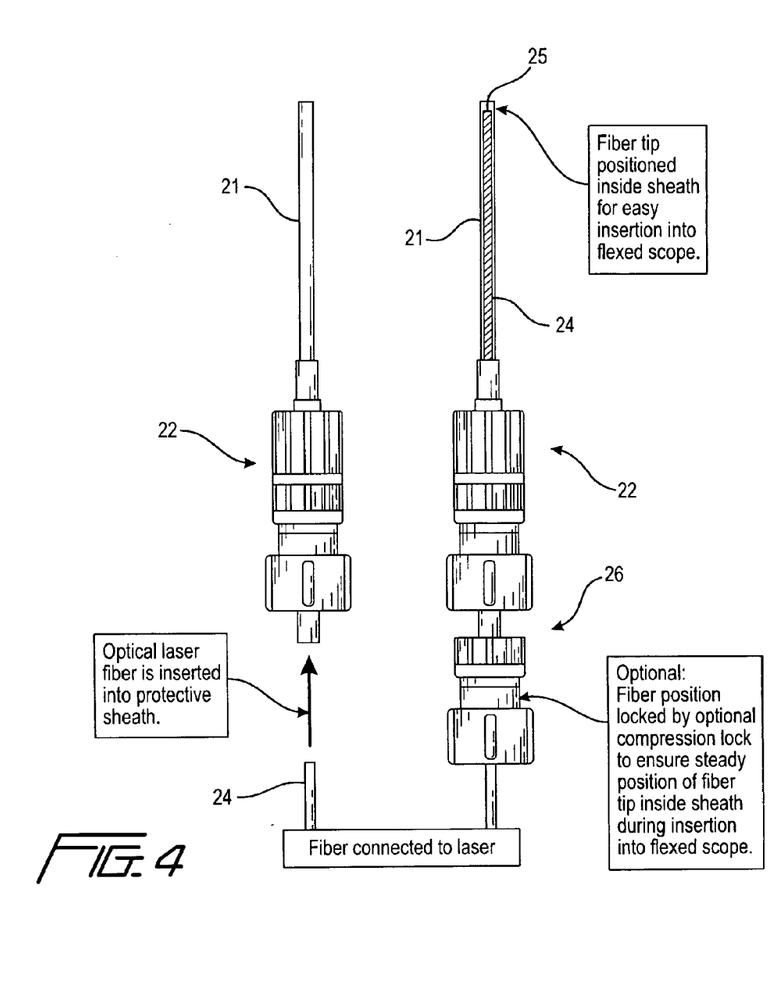
FIGS. 4-6 illustrate a method of using the protective sheath of FIG. 3.
Figure 5:
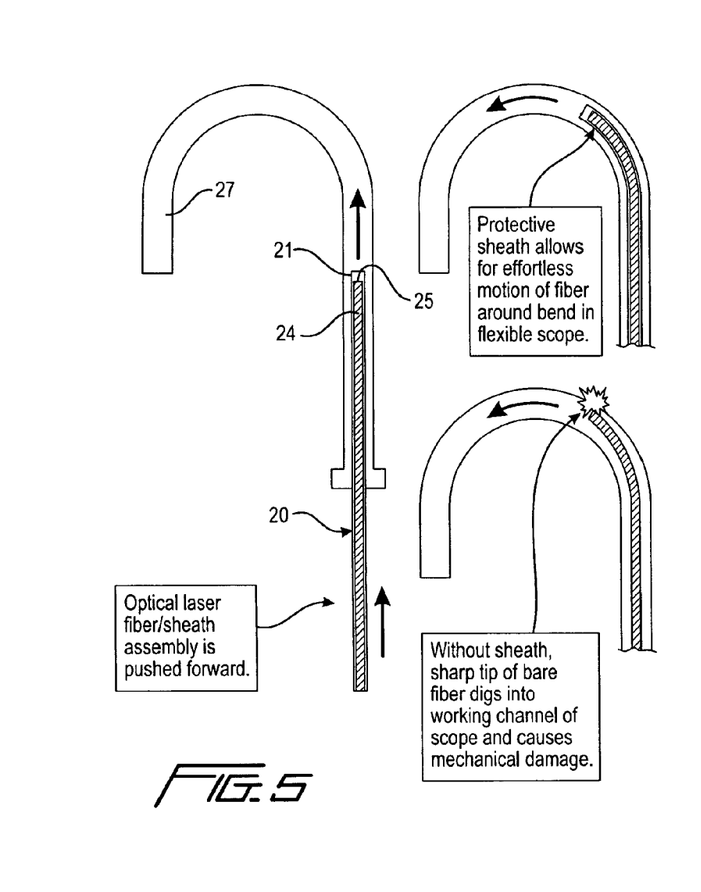
Figure 6:
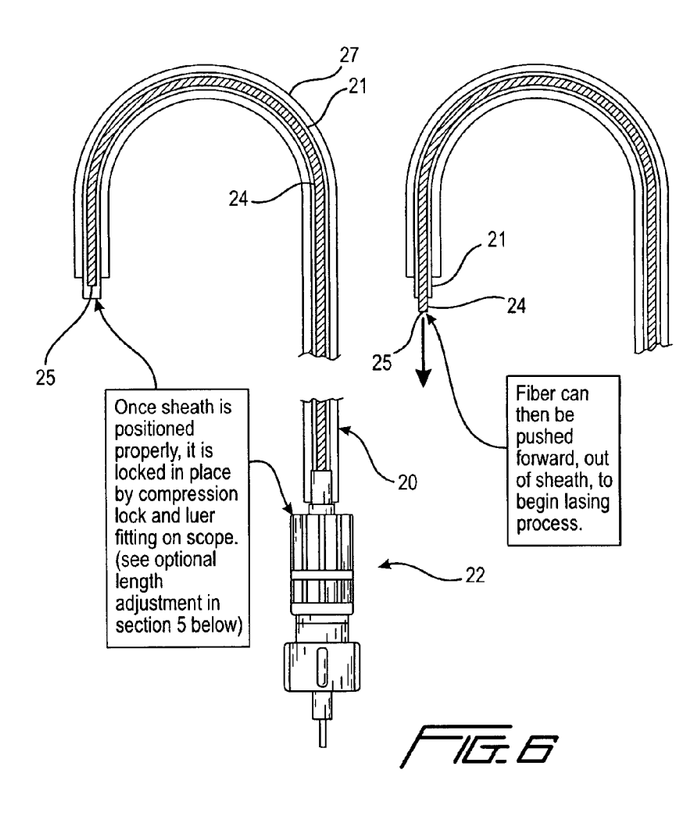

FIGS. 4-6 illustrate a preferred method of using the sheath of FIG. 4. First, as shown in FIG. 4, an optical laser-delivery fiber 24 is inserted into the protective sheath 20 until the tip 25 of the fiber reaches a position near the end of the sheath, after which the fiber position is locked by an optional compression lock 16 or other fitting to ensure steady position of the fiber tip inside the sheath during insertion into a flexed scope 27.

Next, as illustrated in FIG. 5, the sheath 20, which contains the optical fiber 24, is then inserted into the working channel of the scope 27, the distal end of which has already been positioned by the operator, the scope guiding the sheath toward the treatment area. Because the sheath 20 is flexible, it can easily follow any bends in the scope as it is pushed toward the treatment area. In addition, because the fiber tip 25 is within the sheath, it can be moved to the treatment site without damaging a wall of the scope due to the sharp tip of the fiber digging into the working channel of the scope and causing mechanical damage.

As illustrated in FIG. 5, once the sheath 20 is positioned properly, it is locked in place by the compression lock and luer fitting on the scope, at which time the fiber 24 can be released with respect to the scope and pushed forward out of the sheath to begin the lasing process.

Figure 7:
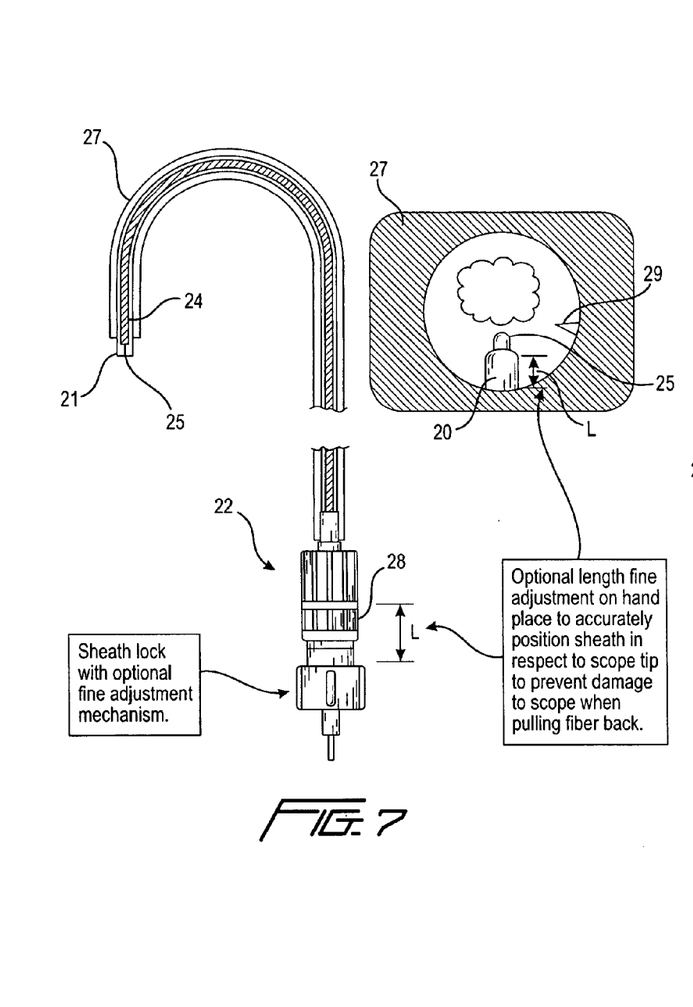
FIG. 7 illustrates an optional additional step to the method of FIGS. 4-6.

Optionally, as illustrated in FIG. 7, the position of the fiber tip 25 may be adjusted using a fine adjustment mechanism 28 on the sheath lock, by moving the sheath with respect to a position indicator 29 in the field of view of the scope, to prevent damage to the scope when pulling the fiber back.

Figure 8:
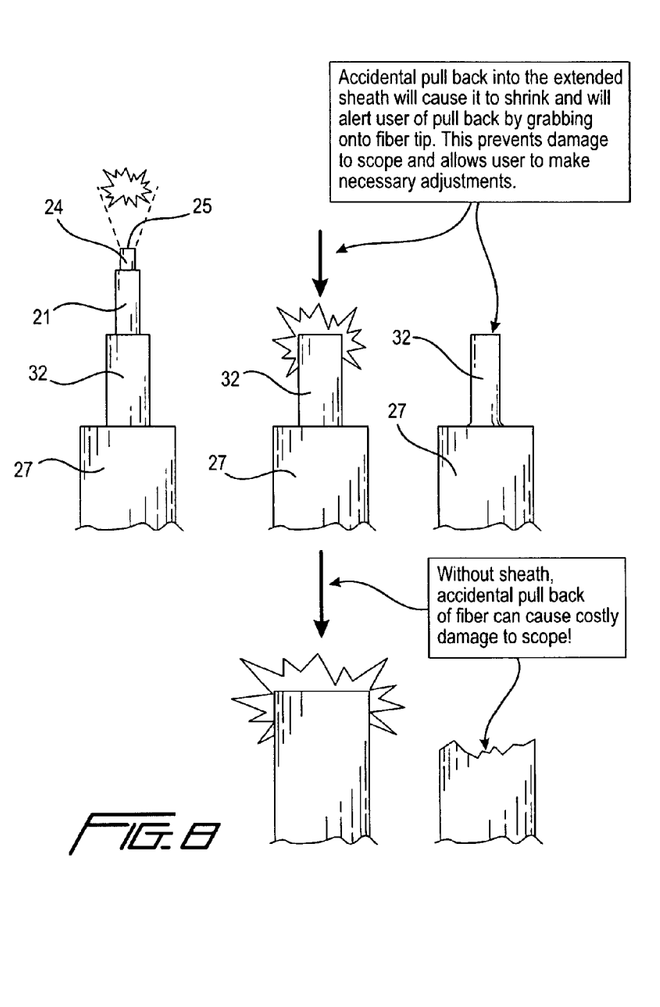
FIG. 8 illustrates an optical heat shrink feature of the protective sheath of FIG. 3.

As illustrated in FIG. 8, the protective arrangement of the preferred embodiment may optionally also include an additional heat shrink feature in the form of a sleeve 32 that shrinks when exposed to high heat resulting from accidental pull back of the fiber tip 25 towards the scope, and thereby grab the sheath and fiber before the fiber tip 25 actually enters the scope, preventing costly damage to the scope.

Figure 9:
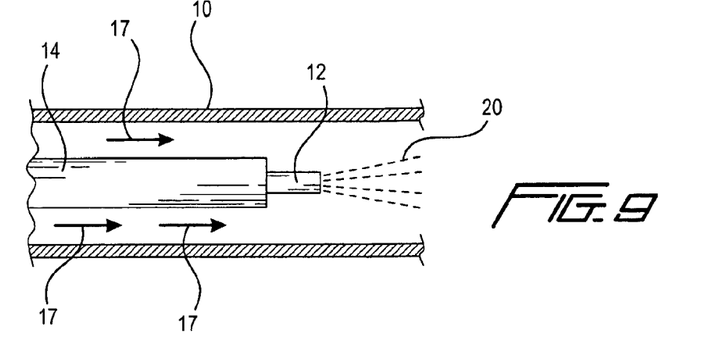
FIGS. 9-10 are cross-sectional views of an introducer, illustrating a problem that can occur when the fiber tip is withdrawn into the introducer.
Figure 10:
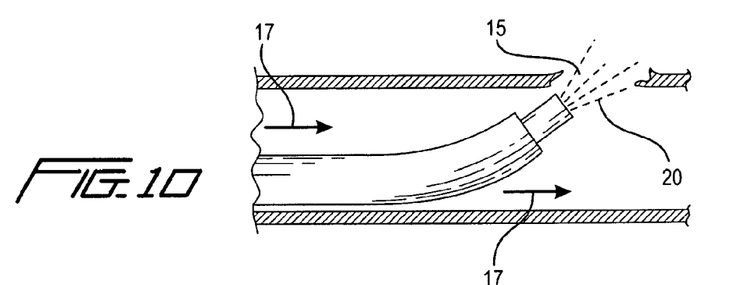

FIGS. 9 and 10 show the manner in which damage is caused by accidental pull-back of the fiber tip into the introducer or scope. As shown in FIG. 9, when water or saline (17) passes through the working channel (10), there is often no damage to the scope even though the fiber tip (12) has been pulled back into the working channel while laser energy (20) is still being emitted. This is because the fiber tip (12) may not be touching the working channel (10), and because the water or saline (17) may absorb at least some of the laser energy (20). However, as shown in FIG. 10, when the fiber tip (12) is in contact with the working channel, the laser energy (20) can blow a hole (15) right through the wall of the working channel (10).

Figure 11:
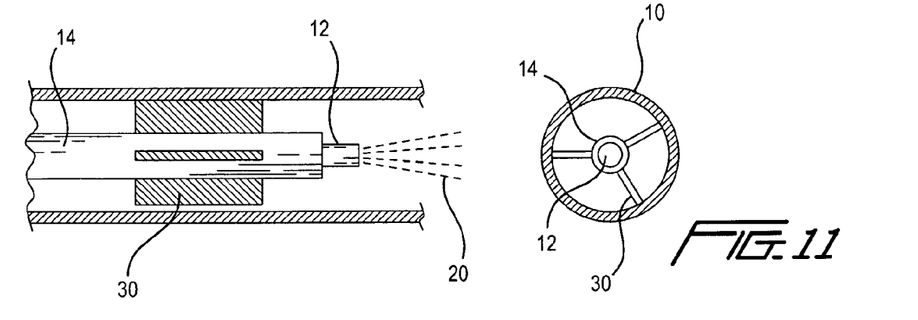
FIGS. 11-12 are cross-sectional views illustrating a solution to the problem of FIGS. 9-10, in which a support guide is added to prevent the fiber tip from touching a wall of the introducer.
Figure 12:
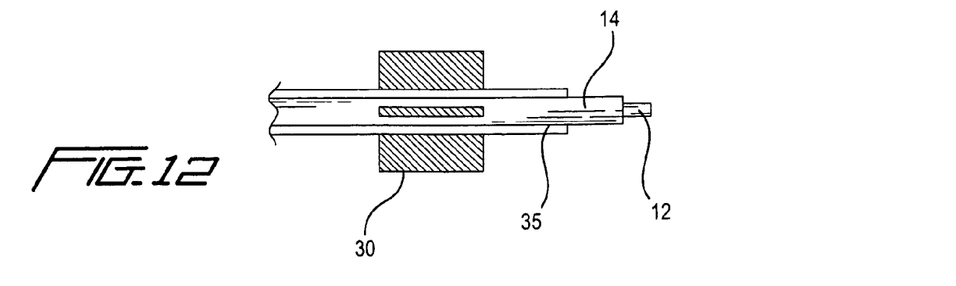

As illustrated in FIGS. 11 and 12, this problem can be solved in two ways. The first, shown in FIG. 11, is to attach a support guide (30) to a outside surface (14) of the fiber tip (12). Alternatively, the support guide (30) may be added to a sheath (35), whether conventional or radiation-absorbing as described above. In either case, the support guide prevents the fiber tip from approaching or contacting the wall of the working channel (10). Mounting of the support guide on the sheath allows the fiber to continue to move within the sheath, with additional protection being possible by adding a fluid to the sheath.

Having thus described various preferred embodiments of the invention in sufficient detail to enable those skilled in the art to make and use the invention, it will nevertheless be appreciated that numerous variations and modifications of the illustrated embodiment may be made without departing from the spirit of the invention. For example, the enhanced monitoring method and apparatus of the invention may be used not only to prevent damage due to burning tissues or instruments, but also to provide protection against heat-related damage due to broken fibers, fiber contact with stones, fiber contact with tissues, fiber contact with surgical instruments (by way of example and not limitation, stainless steel scopes), fiber contact with stone baskets, graspers, coils, etc., failure of the fiber connector, and end-of-life failure of reusable fibers. Furthermore, in addition to using a sacrificial coating as a

"canary in the coalmine," i.e., to provide early warning of overheating problems, the monitoring methods and apparatus of the invention may modify coatings that are already on the instruments, such as the Nitinol™ coatings provided over the wires of Boston Scientific's stone cone, to enhance detection of fiber/laser contact. It is therefore intended that the invention not be limited by the above description or accompanying drawings, but that it be defined solely in accordance with the appended claims.

I claim:

1. Apparatus for therapeutic application of energy to a tissue, comprising:
    a delivery fiber arranged to deliver optical energy from a laser to a treatment site at a distal end of the delivery fiber; and
    a feedback circuit including a detector arranged to detect overheating of, or damage radiation emitted by, at least one of: (a) an instrument used in said therapeutic application of energy and (b) said tissue; and
    a sacrificial element situated near the distal end of the fiber for amplifying or enhancing detectability of overheating or damage radiation by absorbing selected wavelengths of said damage radiation so as to cause sacrifice of the sacrificial element during delivery of optical energy to the treatment site, said sacrificial element being made of a sacrificial material that absorbs said specific wavelengths and, in response to the absorption of said specific wavelengths emits radiation in the form of visible light as it is sacrificed, said radiation emitted by the sacrificial material having an increased contrast with respect to background radiation than said damage radiation so that the overheating or damage radiation can more easily be detected before damage to the instrument or tissue occurs.

2. Apparatus as claimed in claim 1, wherein said sacrificial element is positioned in a working channel of an endoscope.

3. Apparatus as claimed in claim 2, wherein said sacrificial element is a coating in said working channel of the endoscope.

4. Apparatus as claimed in claim 2, wherein said sacrificial element is a sleeve positioned in the working channel of the endoscope.

5. Apparatus as claimed in claim 1, wherein said sacrificial element is sheath made up of a flexible tubing surrounding said fiber.

6. Apparatus as claimed in claim 5, wherein said flexible tubing is made of polyimide.

7. Apparatus as claimed in claim 5, wherein said flexible tubing is made of polyethylene terephthalate (PET).

8. Apparatus as claimed in claim 5, wherein a thickness of said flexible tubing is substantially less than 0.5 mm, whereby said tubing does not interfere with insertion of said tubing into a pre-bent endoscope or with flow of irrigation fluid past the tubing during a laser treatment.

9. Apparatus as claimed in claim 5, wherein said flexible tubing is a heat shrink tubing configured to shrink as a result of an increase in temperature that occurs when the fiber tip is pulled back toward the endoscope while laser energy is being supplied through the fiber, wherein the shrinkage causes the tubing to hold the fiber and prevents the fiber tip from being pulled into the endoscope while the laser energy is being supplied.

10. Apparatus as claimed in claim 5, wherein the sheath further includes holes or perforations along its length to allow for better gas sterilization and aid in providing fluid access and ease movement of the fiber within the sheath.

11. Apparatus as claimed in claim 1, further comprising a support guide mounted on an exterior of said sacrificial element to prevent a tip of said fiber from contacting a wall of a working channel through which said fiber has been inserted.

12. Apparatus as claimed in claim 1, wherein delivery fiber is a bare fiber and said detector is positioned on said bare fiber.

13. Apparatus as claimed in claim 1, wherein a surface of said instrument used in said therapeutic application of energy is arranged to enhance detection of said damage radiation.

14. Apparatus as claimed in claim 13, wherein said surface has a color that increases contrast and/or minimizes reflections to increase a probability of detecting the damage radiation or radiation emitted by said sacrificial element.

15. Apparatus for therapeutic application of energy to a tissue, comprising:
    a delivery fiber arranged to deliver optical energy from a laser to a treatment site at a distal end of the delivery fiber; and
    a feedback circuit including a detector arranged to detect overheating of, or damage radiation emitted by, at least one of: (a) an instrument used in said therapeutic application of energy and (b) said tissue,
    wherein a surface of an instrument used in said therapeutic application of energy is arranged to enhance detection of damage radiation by absorbing selected wavelengths of heat energy included in said damage radiation, said damage radiation being emitted by at least one of: (a) said instrument and (b) said tissue, said surface being made of a sacrificial material that absorbs said specific wavelengths and, in response to said absorption of specific wavelengths, emits radiation in the form of visible light as the surface of the instrument is sacrificed, and said radiation emitted by the surface having an increased contrast with respect to background radiation than said damage radiation so that the overheating can more easily be detected before damage to the instrument occurs.

16. Apparatus as claimed in claim 15, wherein said surface has a color that increases contrast and/or minimizes reflections to increase a probability of detecting the damage radiation or radiation emitted by said sacrificial element.

* * * * *